United States Patent [19]

Sawyer et al.

[11] Patent Number: 4,722,725
[45] Date of Patent: Feb. 2, 1988

[54] METHODS FOR PREVENTING THE INTRODUCTION OF AIR OR FLUID INTO THE BODY OF A PATIENT

[75] Inventors: Philip N. Sawyer, Brooklyn; Joseph F. Fitzgerald, Queens, both of N.Y.

[73] Assignee: Interface Biomedical Laboratories, Inc., Brooklyn, N.Y.

[21] Appl. No.: 53,495

[22] Filed: May 11, 1987

Related U.S. Application Data

[63] Continuation of Ser. No. 818,434, Jan. 13, 1986, abandoned, which is a continuation-in-part of Ser. No. 484,205, Apr. 12, 1983, Pat. No. 4,684,364, and a continuation-in-part of Ser. No. 511,256, Jul. 6, 1983, Pat. No. 4,568,333.

[51] Int. Cl.⁴ .................................... A61M 5/00
[52] U.S. Cl. .................................... 604/27; 604/122; 604/44; 604/167
[58] Field of Search .................... 604/122, 27, 28, 30, 604/43–45, 167–170, 247, 52, 53, 129

[56] References Cited

U.S. PATENT DOCUMENTS

| | | | |
|---|---|---|---|
| 220,559 | 10/1979 | Wilson | 137/843 |
| 1,696,018 | 12/1928 | Schellberg | 604/43 |
| 2,786,642 | 3/1957 | Comb | 251/50 |
| 2,988,103 | 6/1961 | Canvasser | 137/218 |
| 3,298,391 | 1/1967 | Savage | 137/493 |
| 3,441,245 | 4/1969 | Holland et al. | 251/5 |
| 3,469,582 | 9/1969 | Jackson | 251/5 |
| 3,543,752 | 12/1970 | Hesse | 604/123 |
| 3,672,372 | 6/1972 | Heimlich | 128/349 R |
| 3,687,365 | 8/1972 | Laessig | 236/99 |
| 3,717,174 | 2/1973 | Dewall | 604/34 |
| 3,769,982 | 11/1973 | Schulte | 128/350 |
| 3,833,013 | 9/1974 | Leonard | 137/171 |
| 3,888,249 | 6/1975 | Spencer | 128/214 R |
| 3,967,645 | 7/1976 | Gregory | 137/525.1 |
| 3,991,768 | 11/1976 | Portnoy | 128/350 V |
| 4,062,360 | 12/1977 | Bentley | 128/276 |
| 4,096,860 | 6/1978 | McLaughlin | 604/44 |
| 4,103,686 | 8/1978 | LeFevre | 128/214 R |
| 4,103,689 | 8/1978 | Leighton | 128/350 V |
| 4,108,175 | 8/1978 | Orton | 604/168 |
| 4,111,047 | 9/1978 | Bailey | 137/843 |
| 4,126,132 | 11/1978 | Portner et al. | 604/123 |
| 4,134,402 | 1/1979 | Mahurkar | 128/214 R |
| 4,300,552 | 11/1981 | Cannon | 128/214 E |
| 4,303,100 | 12/1981 | Kalb | 251/5 |
| 4,324,239 | 4/1982 | Gordon et al. | 128/214 R |
| 4,336,800 | 6/1982 | Giovanni | 604/123 |
| 4,385,631 | 5/1983 | Uthmann | 604/284 |
| 4,468,224 | 8/1984 | Enzmann et al. | 604/247 |
| 4,496,350 | 1/1985 | Cosentino | 604/175 |
| 4,501,531 | 2/1985 | Bilstad et al. | 604/123 |
| 4,502,502 | 3/1985 | Krug | 604/247 |
| 4,515,589 | 5/1985 | Austin et al. | 604/122 |
| 4,535,773 | 8/1985 | Yoon | 604/169 |
| 4,535,818 | 8/1985 | Duncan | 137/846 |
| 4,540,027 | 9/1985 | Forberg | 604/247 |
| 4,568,333 | 2/1986 | Sawyer et al. | 604/122 |

FOREIGN PATENT DOCUMENTS

| | | | |
|---|---|---|---|
| 1052659 | 4/1979 | Canada . | |
| 2513490 | 10/1975 | Fed. Rep. of Germany | 604/5 |
| 0592193 | 7/1925 | France | 604/44 |
| 1510191 | 5/1978 | United Kingdom . | |
| 509746 | 6/1969 | U.S.S.R. | 137/843 |
| 555251 | 6/1977 | U.S.S.R. . | |

Primary Examiner—Stephen C. Pellegrino
Attorney, Agent, or Firm—Pennie & Edmonds

[57] ABSTRACT

Methods for preventing the introduction of air into the vascular system of a patient during intravenous or intra-arterial procedures, as well as for preventing the reflex of fluids into the body of a patient. Also, novel fluid directing means and catheters which include integral or attached fluid flow control means for use in these methods.

33 Claims, 20 Drawing Figures

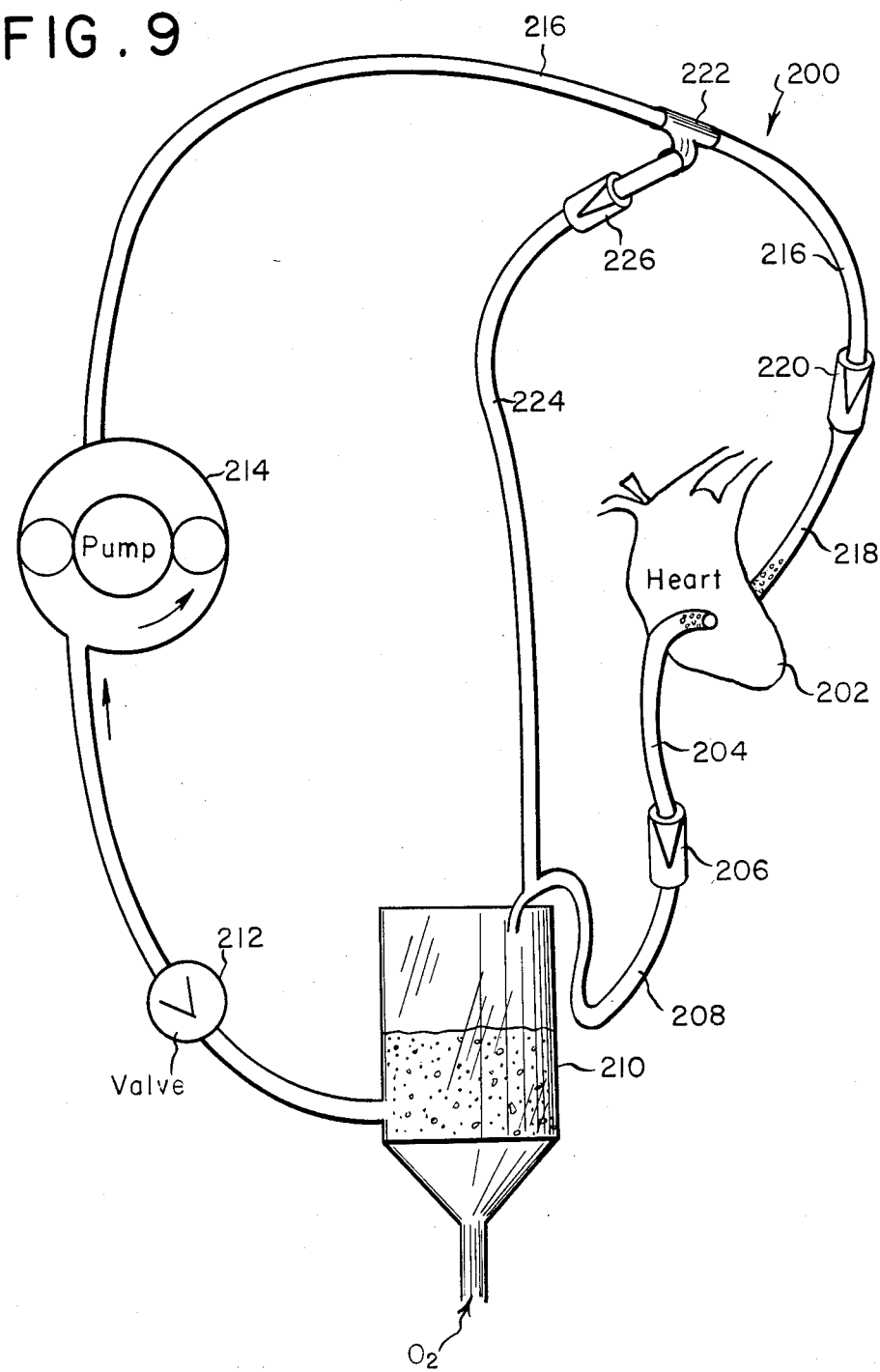

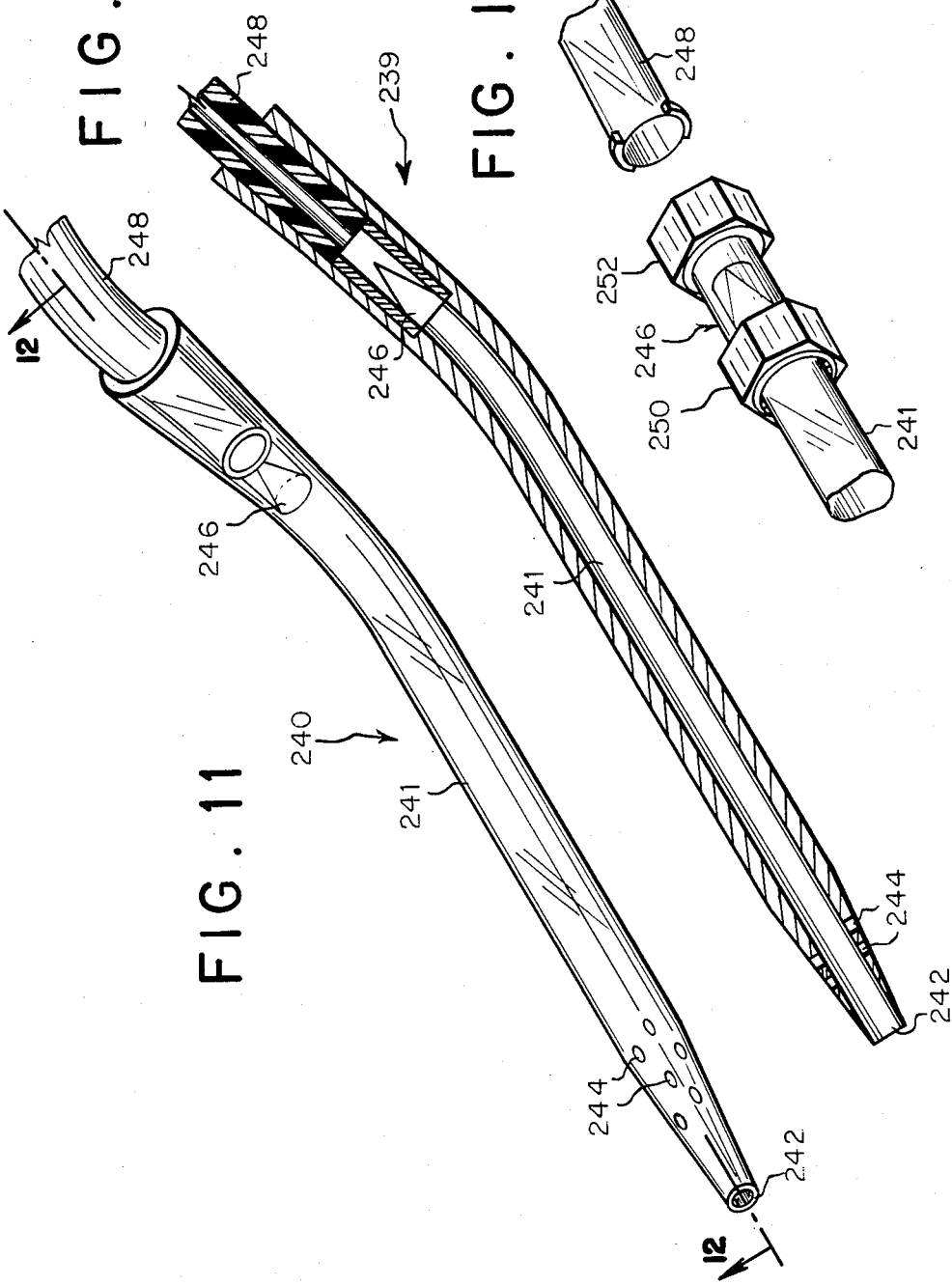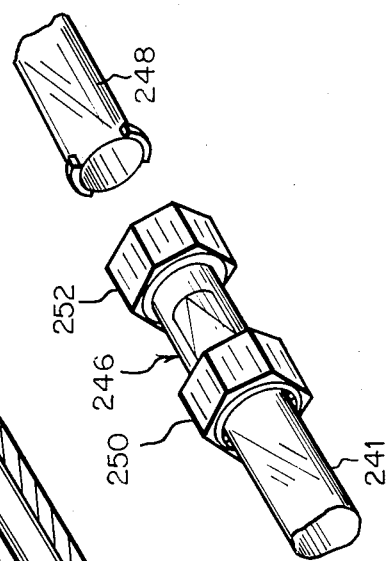

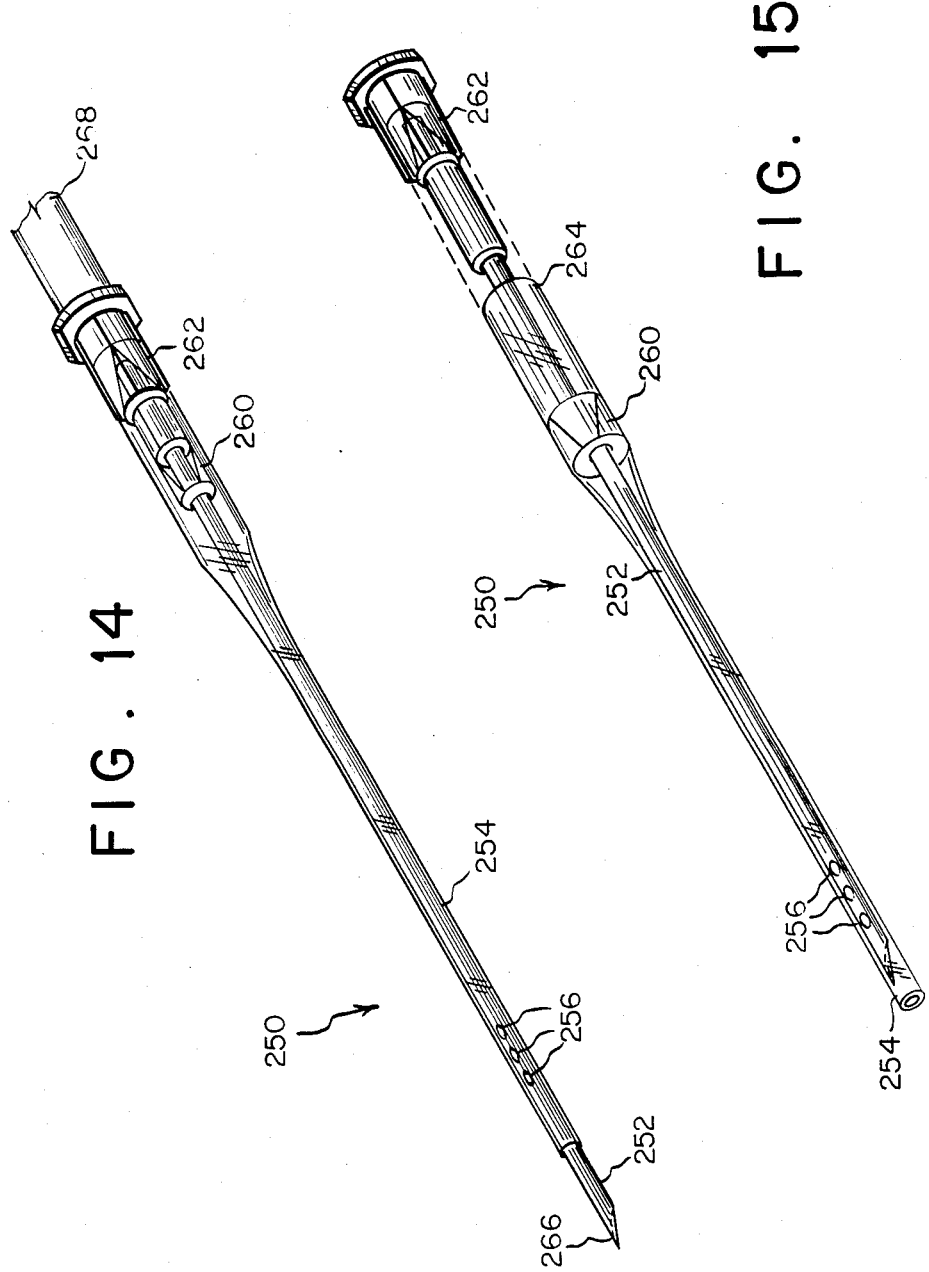

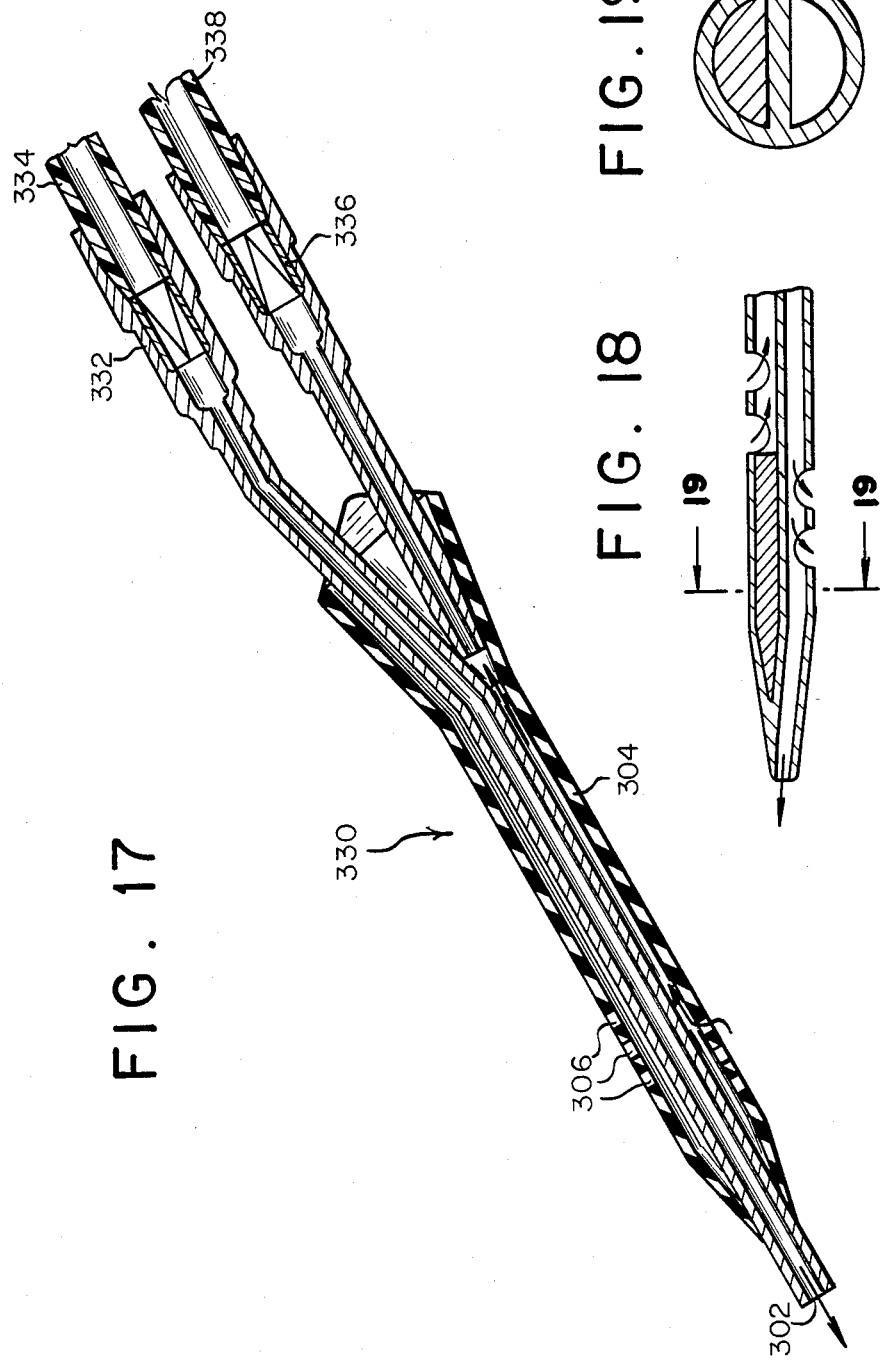

METHODS FOR PREVENTING THE INTRODUCTION OF AIR OR FLUID INTO THE BODY OF A PATIENT

CROSS-REFERENCE TO RELATED APPLICATIONS

This is a continuation of application Ser. No. 818,434, filed Jan. 13, 1986, now abandoned, which is a continuation-in-part of application Ser. No. 484,205, filed Apr. 12, 1983 now U.S. Pat. No. 4,684,364, and a continuation-in-part of application Ser. No. 511,256, filed July 6, 1983, now U.S. Pat. No. 4,568,333.

TECHNICAL FIELD

This invention relates to methods for preventing the entry of air into the vascular system of a patient during intravenous or intra-arterial procedures. Also, the invention relates to methods for preventing the reflux of fluids, such as urine, back into the body of the patient when such fluids are removed by catheter means.

BACKGROUND

Procedures have long been known involving the introduction or removal of fluids into or from the vascular system or body cavity of a patient. For the introduction of fluids, these have developed to a point of employing a source of fluid for intravenous procedures and connecting such source, often via a pump, through a needle or catheter into the vascular system. The pump itself has been developed to a point that when connecting catheters are accidentally opened to ambient atmosphere, the pumping operation is terminated thereby to reduce the possibilities of air being introduced into the vascular system. This is necessary because the introduction of air will cause an embolism which in turn may be fatal to the patient being treated. Nevertheless, the use of such a pump, which is commercially available, is not always effective to prevent accidents of the aforenoted type in all cases. Thus, for example, when the intravenous tubing is coupled to a catheter situated on the downstream side of the pump, and this catheter becomes accidentally opened to ambient atmosphere, the pressure differential between ambient atmosphere and the vascular system in which the distal tip of the catheter resides (particularly in the chest and/or abdomen) is such as to cause air to be sucked through the catheter into the vascular system. Also, when the fluid is introduced by gravity flow, this problem can result from an accidental opening or separation of the cathether or the fluid supply. This accidental occurrence has been known to cause serious harm or death to the patient being treated.

A number of patents have been found which attempt to resolve problems of the aforenoted type, as well as to related systems exposed to pressure differential or the like. These patents include U.S. Pat. Nos. 2,538,662; 3,570,808; 3,599,670; 3,888,249; 4,103,686; 4,252,166; 4,324,239 and 4,335,747.

Abbott in U.S. Pat. No. 2,538,662 discloses a surgical apparatus for the intravenous administration of liquids, such as whole blood, blood plasma, dextrose solutions, and the like and is directed particularly to an expendable valve unit construction used in such surgical apparatus.

Wren in U.S. Pat. No. 3,570,808 discloses a coupling assembly for releasably attaching an air hose to a regulator of the type used in conjunction with the face mask of an underwater diving apparatus. The coupling is readily detachable and a valve mechanism is provided so that when the air hose is decoupled from the regulator underwater, the valves provided in the regulator air inlet and in the end of the air hose are immediately biased to a closed position. Such a construction and arrangement may have utilization in connection with intravenous procedures.

Simon in U.S. Pat. No. 3,595,228, discloses a portable alarm device attached to a coupling in a therapeutic apparatus to provide an alarm to alert hospital personnel under certain dangerous conditions as might apply to a respirator flow line or a tracheostomy tube assembly for indicating a break therebetween.

In U.S. Pat. No. 3,599,670, Gurner discloses a fluid coupling with a valve means having such provision that if a maximum rate of flow through a hose is exceeded as, for example, by leakage, the coupling valve will close and prevent further flow.

In U.S. Pat. No. 3,888,249, Spencer discloses a catheter for prolonged infusion of medication into an artery. The catheter is provided with a tip design employing a flap valve principle to assure uniform and steady diffusion of the medication into the blood stream and to inhibit retrograde flow of blood into the catheter thereby to minimize clotting in the catheter and blockage of medication flow.

Harverland discloses in U.S. Pat. No. 3,906,034 a pressure sensor-timer alarm for pressure sensitive devices wherein a plunger, having a magnetically mounted switch actuator, actuates a switch in response to pressure changes from a diaphragm. A failure to actuate the switch in either phase of the breathing cycle within a preset time causes the actuation of an alarm.

Winicki discloses in U.S. Pat. No. 4,067,329 a warning device which is actuated by the disconnection of a tube from another tube such as, for example, of a respirator cannula from a patient's medical apparatus.

In U.S. Pat. No. 4,103,686, LeFevre discloses a dual valve assembly for intravenous infusions from multiple parenteral fluid sources. The assembly controls forward and reverse flow through a flow line and includes normally seated first and second valves mounted for movement toward and away from respective valve seats to control flow in such a manner as to prevent reverse flow through the assembly.

Gordon shows in U.S. Pat. No. 4,324,239 a safety valve for preventing air embolism and hemorrhage. The safety valve disclosed is useful for catheterization procedures and is characterized by a piston having an internal flow path and so arranged as to be biased to a closed position. The arrangement is such as to prevent air embolism and hemmorhage.

In U.S. Pat. No. 4,335,747, Mitsumoto et al. disclose an arrangement which is effective to exclude air or other undesirable gas in a connecting procedure.

None of the aforegoing patents, nor any of the other arrangements known heretofore, however, is as effective as the present invention for preventing the introduction of air into the vascular system of a patient, or for preventing the reflux of fluids back into the organ or portion of the body from which such fluids were removed.

SUMMARY OF THE INVENTION

It is an object of the invention to provide improved methods for preventing the introduction of air into the vascular system of a patient during various intravenous or intra-arterial procedures and during cardio-pulmonary bypass.

Another object of the invention relates to a method for preventing the reflux of fluids which have drained or removed from an organ or the pleural cavity of the body.

Still another object of the invention is to provide improved methods for introducing fluids into the vascular system of a patient in the situation wherein the relative negative pressure in a receiving body effectively constitutes a vacuum or suction which would tend to draw therein air from the ambient atmosphere.

Thus, the invention relates to a method for preventing the introduction of ambient air into the vascular system of a patient when catheter means is introduced into the vascular system during intravenous or intra-arterial procedures which comprises providing the catheter means with fluid flow control means which remains competent in response to ambient air pressure but which opens in response to a positive fluid pressure above that of ambient air. This fluid flow control means is integral with or attached to the catheter means. Also, the method further comprises utilizing means to maintain the fluid flow control means in an open position to view blood reflux through the catheter means or to facilitate the introduction of obturating means. The means to maintain the fluid flow control means in an open position may be a second fluid flow control means which remains competent in response to ambient air pressure but which opens in response to a positive fluid pressure above that of ambient air. Preferably, the obturating means comprises second catheter means, trocar means, needle means, or fluid directing means.

The invention also relates to a method for preventing the reflux of blood from the vascular system of a patient into catheter means introduced into the vascular system during intravenous or intra-arterial procedures which comprises providing the catheter means with fluid flow control means which remains competent in response to blood reflux and ambient air pressure, but which opens in response to a positive fluid pressure above that of ambient air. This method also contemplates utilizing means to maintain the fluid flow device in an open position to temporarily view blood reflux through the catheter means or to facilitate the introduction of obturating means, trocar means, second catheter means, or fluid directing means into the first catheter means. Again, the means to maintain the fluid flow control means in an open position further comprises a second fluid flow control means which remains competent in response to blood reflux and ambient air pressure, but which opens in response to a positive fluid pressure above that of ambient air. The maintaining means may be connected to exterior conduit means such that, in the event the exterior conduit means is disengaged from the patient, the maintaining means is also removed, thus returning the fluid flow control means to a closed position.

Another aspect of the invention relates to a method for preventing the reflux of fluids into an organ or the pleural cavity of a patient when fluid directing means are utilized for the removal of said fluids from the patient. This method comprises providing the fluid directing means with fluid flow control means which remains competent in response to fluid reflux but which opens in response to fluid pressure in the patient to facilitate for removal of said fluids. This method further comprises periodically utilizing means to maintain the fluid flow said device in an open position to facilitate faster removal of said fluids from the patient.

The methods of the invention advantageously utilize catheter means comprising an elongated body portion for insertion into a patient; at least one integral hub portion adjacent to the body portion; and at least one fluid flow control means located in the body or hub portion or adjacent to the hub portion. The fluid flow control means remains competent in response to ambient air pressure but which opens in response to a positive fluid pressure above that of ambient air, and may be either integral with or releasably secured to the hub portion. Where two integral hub portions are provided, each hub includes fluid flow control means located adjacent thereto, and each fluid flow control means may be integral with or releasably secured to its respective hub portion.

In a preferred embodiment, a first hub portion allows the introduction of a fluid into the body of the catheter means and a second hub portion allows a body fluid to be removed from the body of the catheter means. To do this, the first hub portion usually includes fluid flow control means which remain competent in response to blood reflux or ambient air pressure but which opens in response to a positive fluid pressure above that of ambient air, while the second hub portion includes fluid flow control means which remains competent in response to fluid reflux but which opens in response to fluid pressure in the patient.

These catheter means may also include obturating means for rendering incompetent the fluid flow control means. Preferably, the obturating means is second catheter means, trocar means, needle means, or fluid directing means. In one arrangement, the obturating means is trocar means which includes a fluid flow control means. In one-embodiment, this flow control means remains competent in response to blood reflux or ambient air pressure but opens in response to a positive fluid pressure above that of ambient air. Alternately, this flow control means may remain competent in response to fluid reflux, but will open in response to fluid pressure in the patient.

The end of the body portion opposite the hub portion normally includes a plurality of apertures. The fluid flow control means is located in the body portion, preferably adjacent to the hub portion.

In achieving the above and other objects of the invention, there is provided various fluid flow means, such as catheter means, which are provided with an integral valves or attached fluid flow control means to either prevent air introduction or fluid reflux into the patient.

In one embodiment, the fluid flow control means comprises a body provided with an input chamber and an output chamber and further provided with respective orifices respectively coupled to the chambers, there being furthermore provided a resilient means associated with the aforesaid body and adapted for defining with the body a connecting channel between the orifices, but normally being configured to obturate the orifice coupled to the output chamber to obturate the latter orifice and such that a relative negative pressure in the output chamber will tend to strengthen the obturating of the latter orifice, whereas a relative positive pressure in the input chamber will tend to open the latter orifice. As a result of this general type of construction, it is possible, in accordance with the invention, to prevent the drawing of air into and through the output chamber while allowing a positive pressure at the input chamber to effect a normal flow of fluid therethrough into the output chamber and, thereafter, into the body of the patient.

The resilient means encircles the orifices and defines therewith, the connecting channel in the form of an annular space. The input and output chambers may, in a preferred embodiment of the invention, be coaxial bore sections with the above-mentioned orifices being radially aligned with respect thereto. The bore sections may, moreover, be parts of a common bore, with means being provided in the bore to isolate the sections from each other.

The body may be configured to define an annular groove bracketed by shoulders, the resilient means being a tube of resilient material supported on and extending between these shoulders. The fluid flow control means may also include means to urge the tube yieldingly against the orifice coupled to the output chamber. This urging means may be, for example, a foam spring in accordance with a preferred embodiment of the invention. The foam spring may be simply a plug or body of foam such as foam rubber or a foamed plastic or the like.

The body may also include a central portion defining the above-mentioned central grooves and the central portion may be of a cross-section having a flat area at which the above-mentioned orifices open. Furthermore, cylindrical portions may be connected to opposite ends of the central portion as described above.

In an alternate embodiment of the invention, there is provided a fluid control means comprising input means and output means each provided with a bore constituting a flow channel and further means adapted for providing a connecting channel between the bores in response to positive pressure in one of the bores, and for collapsing and thereby obturating the connecting channel in response to a pressure in one of the bores which is negative relative to ambient atmospheric pressure.

The input, output and further means mentioned above are parts of a tubular structure, and the tubular structure is monolithic. The tubular structure may preferably be formed of a resilient material and, even more preferably, of a silicone rubber or the like.

Preferably, a clip arrangement is employed in conjunction with the further means mentioned above to yieldably constrain the same to a flattened shape. A relatively rigid support tube may be provided having spaced ends and being provided with a bore within which the aforesaid tubular structure is partly accommodated. The tubular structure may preferably include end portions extending out of the support tube and being rolled back along the support tube ends for engagement therewith. Preferably, the input and output means taper towards the further means.

There is also provided a housing provided with first and second channels of different diameters in coaxial relationship to define a shoulder therebetween. The support tube and tubular structure are accommodated in the first channel and a plug means is insertable into the first channel to trap the support tube and tubular structure against the shoulder. In accordance with a specific arrangement, the fluid flow control means is attached to a catheter, which is accommodated in the second channel. The plug and catheter provide passageways coupled through the aforesaid tubular structure. A needle for insertion into the vascular system may be coupled to the catheter in some instances, but in other instances the opposite end of the catheter itself is introduced into the vascular system.

Another aspect of the invention relates to an intravenous system comprising a source of intravenous fluid, a needle or catheter for insertion into the vascular system of a patient, and means for urging the fluid from the source to the catheter to facilitate delivery of fluid to the patient. Fluid directing means can also be used between the source of fluid and the needle or catheter. In conjunction with the foregoing, fluid flow control means is provided in at least the needle or catheter to prevent movement of air therethrough upon an opening of the needle or catheter to ambient atmosphere. Also, a second fluid flow control means can be provided in the fluid directing means.

An alternate embodiment of the intravenous system comprises a source of intravenous fluid, first catheter means for insertion into the vascular system of a patient, a pump for performing a pumping operation and urging the fluid from the source to the first catheter, and second catheter means coupling the pump to the source and to the first catheter. The pump includes means to terminate the pumping operation upon an opening of the fluid source or second catheter to ambient atmosphere. In conjunction with the foregoing, a fluid flow control means is provided in the first catheter downstream of the pump to prevent movement of air therethrough upon an opening of the first catheter to ambient atmosphere.

BRIEF DESCRIPTION OF THE DRAWINGS

The nature, advantages, and various other additional features of the invention will appear more fully upon consideration of the illustrative embodiment now to be described in detail in connection with the accompanying drawing figures, wherein:

FIG. 9 is a generally pictorial illustration of a blood circulation system typically utilized in conjunction with open-heart surgery;

FIG. 11 is a perspective view of a catheter for draining fluids from the body;

FIG. 12 is a cross sectional view taken along lines 12—12 of FIG. 11;

FIG. 13 is a perspective view partially broken away of an alternate arrangement for the end of the catheter of FIGS. 11 and 12.

FIGS. 14 and 15 are perspective views of a catheter and trocar arrangement according to the invention;

FIG. 17 is a cross-sectional view of a cannula similar to that of FIG. 16 but having an integral fluid flow control means;

FIGS. 18 and 19 are views of an alternate embodiment for the tip of the cannula of FIGS. 16 and 17.

DETAILED DESCRIPTION OF THE PREFERRED EMBODIMENTS

Figure 1:
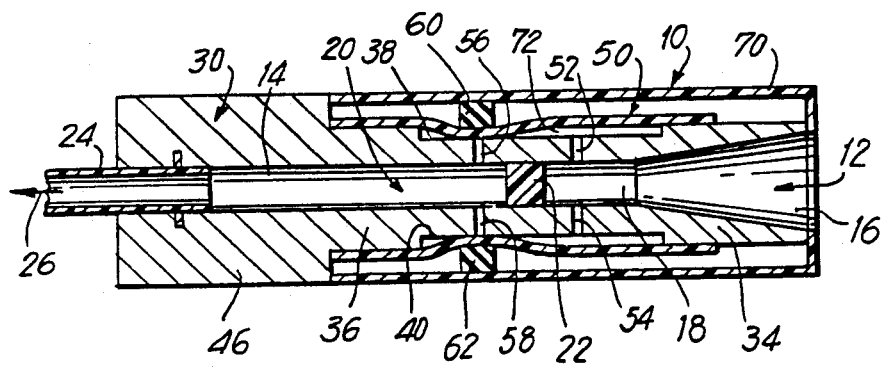
FIG. 1 is an axial cross-section of the valve provided in accordance with a preferred embodiment of the invention. The illustration being partly diagrammatic in nature.
Figure 2:
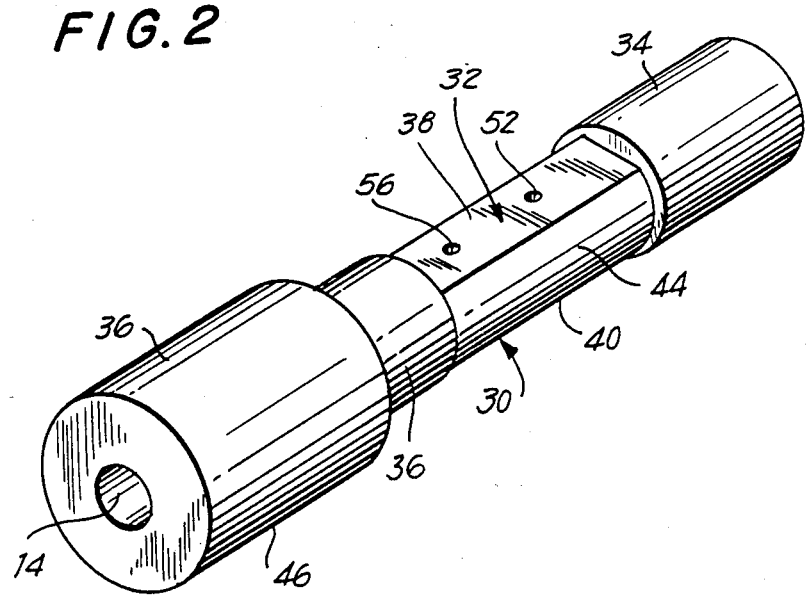
FIG. 2 is a prospective view of a portion of the construction illustrated in FIG. 1.

FIGS. 1 and 2 generally illustrate a fluid flow control means in the form of a valve arrangement 10 provided with an inlet chamber 12 and an outlet chamber 14. The inlet chamber 12 comprises a conical section 16 and a bore of circular cross-section as indicated at 18. The bore section 18 is connected to a bore section constituting the outlet chamber 14. As a matter of fact, these two bore sections are parts of a common bore 20 which is preferably of circular cross-section and of continuous diameter throughout. A plug 22 of plastic may be employed to isolate the bore sections from one another for purposes to be described hereinbelow. A catheter, such as indicated at 24, may be inserted into the outlet chamber 14 to lead fluid therefrom in a direction generally indicated by arrow 26.

The bore 20, mentioned above, is defined internally within a solid relatively rigid body indicated at 30. This body consists of a central portion 32 mounted between and solid with two end portions 34 and 36 which are preferably cylinders of circular cross section.

The central portion 32 comprises two flat surfaces 38 and 40 onto which open the various radilly disposed orifices to be detailed hereinbelow. The central portion 32 moreover comprises two curved sides one of which is visible in FIG. 2. This side is indicated at 44.

The body 30, as illustrated in FIG. 2, may further comprise the enlarged portion 46 as appears in FIG. 1. The cylindrical portions 34 and 36, however, constitute shoulders at opposite ends of the central portion. Upon these shoulders is accommodated a flexible resilient tube such as indicated at 50. This resilient tube rests upon the aforesaid shoulders and its function is to provide the selective obturating of various of the orifices as will be explained hereinafter. These orifices appear in FIG. 1 at 52, 54, 56 and 58. As has been mentioned hereinabove, these orifices are radially disposed relative to the axis of the device being described. They open on the flat surfaces 38 and 40.

In the vicinity of the orifices 56 and 58 are provided two devices 60 and 62 the purpose of which is to deform the resilient tube 50 inwardly and hold the same against the orifices 56 and 58 thereby to normally block the same. The devices 60 and 62 are effectively resilient springs and may be formed, for example, of plugs of a resilient material such as foam rubber or plastic. Their purpose is to yieldingly resist a pressure which might uncover the orifices 56 and 58 other than as described hereinbelow.

Completing the aforesaid structure is a cover tube 70 of relatively rigid material. This tube or cover may be formed of any suitable plastic.

In operation, a particular use is made of an annular space 72 which is defined by the resilient tube 50 relative to the central portion 32 of the body 30. In particular, fluid flowing into the inlet chamber 12 will pass via orifices 52 and 54 into the annular space 72 and then towards the orifices 56 and 58. The normal pressure of the fluid entering the annular chamber or space 72 will be effective to overcome the resistance of spring elements 60 and 62 thereby to uncover orifices 56 and 58. As a result, the fluid will flow into outlet chamber 14 and thence via catheter 24 in the direction indicated at 26.

Assuming that the catheter 26 is implanted into a patient, a negative pressure may appear at the downstream end of the catheter 24 thereby constituting a vacuum or negative pressure applied to the outlet chamber 14. It is desired that this negative pressure not be permitted to draw air through the valve arrangement 10 into the patient's vascular system or body. This possible activity is prevented by the fact that the normal strength of foam springs 60 and 62 will maintain the resilient tube 50 in proximity of the orifices 56 and 58 such that the suction will draw this resilient tube tightly against the orifices 56 and 62 thereby to obturate these orifices and terminate flow through the same.

Should the inlet chamber 12 be detached from the source of pressure (i.e. an infusion pump or the like) there will then be inadequate pressure to cause the fluid to oppose the action of springs 60 and 62 and the vacuum action as mentioned above will maintain orifices 56 and 58 tightly sealed whereupon it will not be possible to draw air into the outlet chamber 14. As a consequence, air flow through the catheter 24 will be automatically prevented.

Thus, there has been described a flow control which comprises a body provided with an input chamber and an output chamber and further provided with respective orifices respectively coupled to these chambers, there being furthermore provided a resilient means associated with the body and adapted for defining with said body a connecting channel between the orifices but normally being configured to obturate the orifice coupled to the output chamber thereby to obturate the latter and such that a relative negative pressure in the output chamber will tend to strengthen the blocking of the output orifices while permitting a relative positive pressure in the input chamber to open the output orifices.

As has been described above, the resilient means is a resilient tube which encircles the above-mentioned body and defines therewith a connecting channel which is in the form of an annular space. As has also been described, the aforesaid body is configured to define an annular groove bracketed by shoulders with the resilient tube being supported on and extending between the shoulders of the body.

In intravenous procedures as may be performed in a hospital for the introduction of a fluid into the vascular system of a patient, there has never been developed a monitoring procedure which will reliably prevent the accidental detachment of a catheter. This usually results in turn in the introduction of air into the vascular system thereby causing harmful embolisms which may in fact result in death or injury to the patient being treated.

In intravenous procedures, the pressure differential between ambient atmospheric pressure and the pressure in an indwelling tube in the vascular system is normally such as to cause air bubbles to be sucked into the vascular system when the associated catheter is inadvertently opened to air. In some known systems, a commercially available pump (Valley Lab I.V. 5000B volumetric infusion pump made by Modern Medical Systems of New Hyde Park, N.Y.) is employed in such a manner that, when the system is opened to ambient atmosphere, the pump terminates its pumping operation. This provision is uniquely important in intravenous procedures, but does not prevent the inadvertent movement of air into the vascular system as may result from the aforenoted pressure differential.

Figure 3:
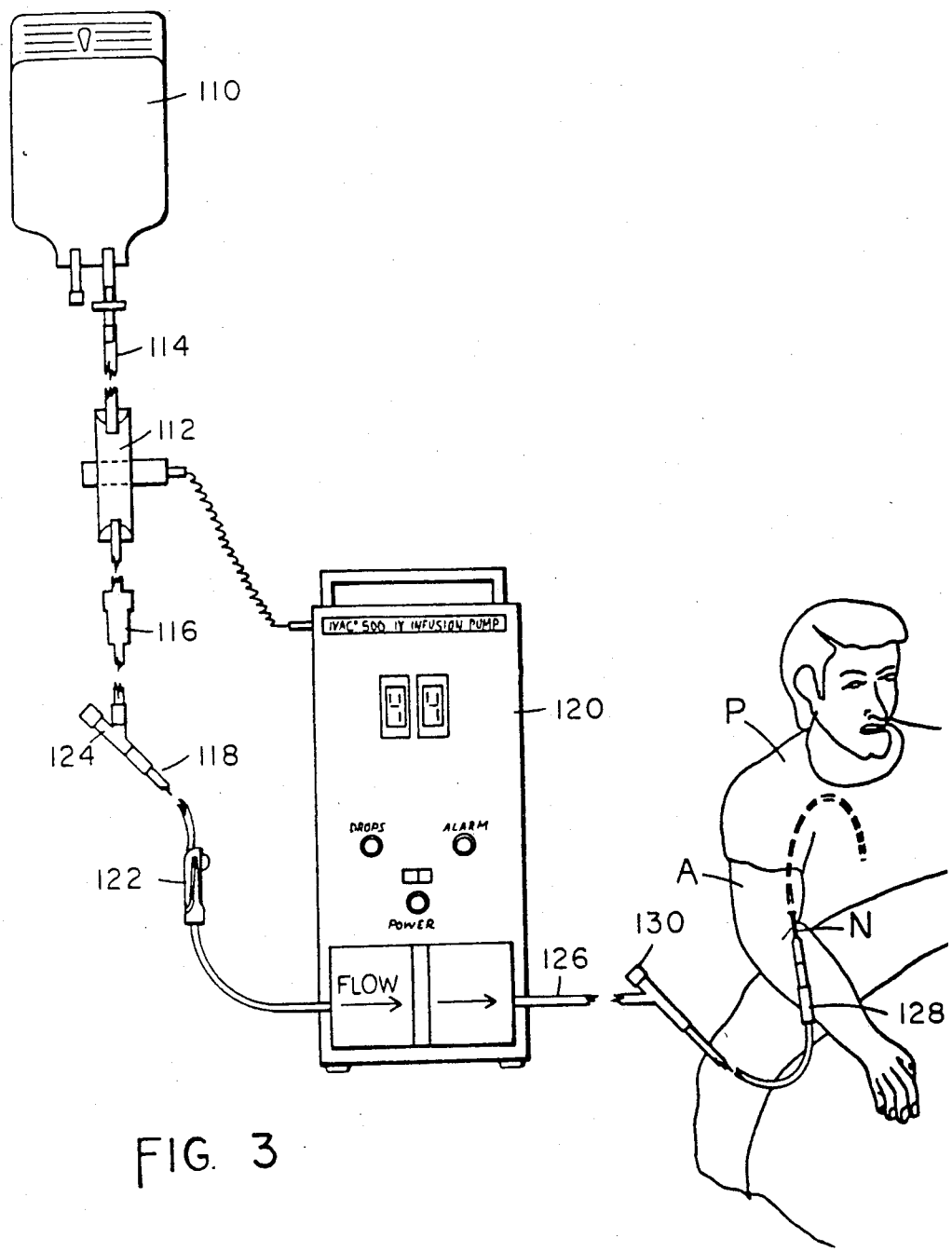
FIG. 3 is a generally pictorial partially broken away view of an intravenous procedure involving a patient and the provisions of the invention.

In FIG. 3 is indicated the physical arrangement necessary for an intravenous procedure as may be performed in a hospital or the like. The patient is indicated generally at P and into the patient's arm A is inserted a needle or catheter N through which the introduction of an intravenous fluid may be effected.

At 110 is indicated a source of intravenous fluid of known type. The source 110 is connected to a reservoir 112 via a catheter 114 with the fluid dripping downwardly drop by drop into the reservoir 112 eventually to be connected via a coupling 116 to a catheter or I.V. tubing 118 feeding into pump 120. A safety arrangement or flow control valve according to the invention may be included at 122 if desired. A spur 124 is indicated for the introduction of medical preparations, nutritional preparations or the like according to well known techniques. The pump 120 is of commercially available type which as aforesaid will terminate operation upon an occurrence of a disturbance such as the detachment of the catheter 118 from the coupling 116.

The pump 120 feeds into an intravenous tubing 126 which in turn is connected via a safety arrangement or flow control valve 128 of the invention to the in-dwelling intravenous catheter N. The tubing 126 may also be provided with a spur 130 which enables the introduction of various types of preparations into the fluid flowing to catheter 126 and via catheter or needle N into the vascular system of patient P.

The function of the safety arrangement is to permit the flow of fluid through the I.V. tubing and into the associated catheter under normal conditions wherein the fluid circuit is closed and is not open to ambient atmosphere. A further function is for this safety arrangement to provide a barrier against the penetration of air from the atmosphere due to differential negative pressure between the vascular system and ambient atmosphere as has been found sufficient to cause the sucking of air bubbles into the vascular system thereby to cause embolism or other harm to the patient being treated.

While one such system has been described in detail relative to the catheter 126 connected downstream of the pump 120 and connected to the needle or catheter N as appears in FIG. 3, it should be noted that in accordance with the invention, more than one such safety arrangement might be employed. Thus, for example, it would be preferred in accordance with the invention if a second such safety arrangement would be provided, for example, in the catheter 118 at position 122 thereby to prevent the sucking of air into the pump 120 thereby to perform in the same manner as has been indicated hereinabove.

Figure 4:
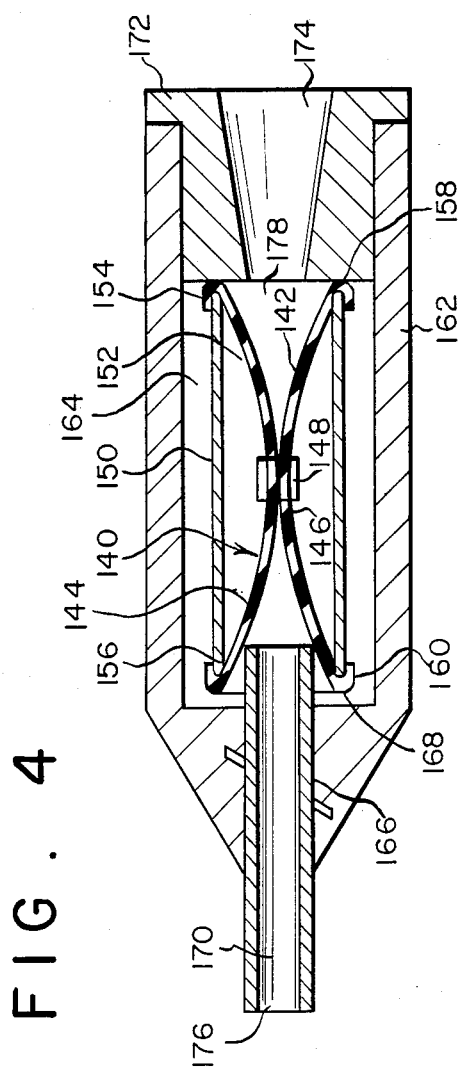
FIG. 4 is an axial section through a flow control valve provided in accordance with a preferred embodiment of the invention.

The structure of the invention also includes a resilient tube formed of silicone rubber or the like which is flexible and deformable and readily responsive to the pressures involved in intravenous procedures. This tube is indicated at 140 in FIG. 4. It includes a upstream portion 142, a downstream portion 144 and a central or coupling portion 146. Portions 142 and 144 taper downwardly towards the central coupling portion 146 which is in flattened condition maintained by a clip arrangement indicated at 148. This clip arrangement may consist of two U-shaped clips which are edge-pinching clips applied to the flattened tubing in a manner to be indicated hereinafter in greater detail. These clips may be formed of plastic or the like and are slipped over the flattened central portion 146 to stay in position thereupon to retain this flattened condition. The clips do not engage completely across the flattened portion of the tubing as will be referred to in greater detail hereinbelow.

A support tube 150 formed of plastic and being relatively rigid is provided to hold in position an accommodate within its bore 152 the tubular structure constituted by the tubing 140. The tube 150 includes two end portions 154 and 156. The end portions 158 and 160 of the tubular structure 140 extend outwardly of the ends 154 and 156 and are rolled backwardly therealong in order to form a coupling between the two components 140 and 150 as a consequence of which a unit is formed which can be easily handled and manipulated during assembly procedures. It will be noted that the tube 140 is a one piece monolithic structure to which detachable clips 148 are applied. The tube 150 is also a monolithic structure to which provides a skeleton or support for the tube 140.

To house the aforegoing unit, there is provided a hub or housing 162 provided with first and second channels 164 and 166. The first channel is of larger diameter than the channel 166 thereby to define therebetween a shoulder 168. A catheter or needle arrangement such as, for example, the catheter 126 has an end portion 170 which is accommodated in the second channel 166. The unit formed by the tube 140 mounted on the tube 150 is accommodated in the first channel 164 and is in abutting relationship with the shoulder 160. A tapered joint plug 172 fits into the channel 164 and is of such a length as to sandwich the afore-described unit against the shoulder 168 to lock the same firmly in position. It will be noted that the plug 172 has a tapered passageway 174 which along with the passageway 176 of end portion 170 of catheter 126, for example, constitutes a continuous passageway with the passageway indicated at 178 relative to the aforesaid tubular structure. The plug 172 is friction welded in position or is otherwise fixed in locking position by bonding means of conventional type suitable for use in conjunction with intravenous procedures. The diameter of the tubular structure and the unit in which it performs is such that the same fits snugly within the channel 164 thereby to assure that fluid flowing through the illustrated structure passes through passageways 174, 178, and 176 in sequence.

Figure 6:
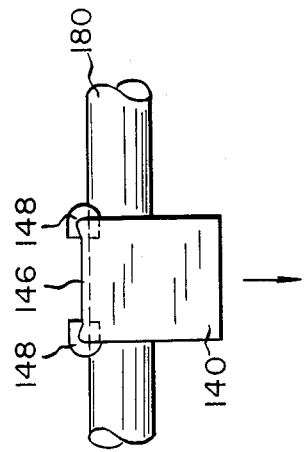
FIG. 6 is a side view corresponding to the illustration in FIG. 5.
Figure 5:
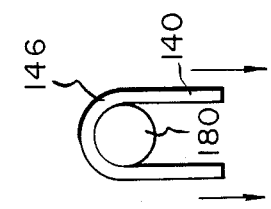
FIG. 5 is a diagrammatic view illustrating a procedural step in the manufacture of the arrangement of FIG. 4.

FIGS. 5 and 6 illustrate the forming of the flattened section 146 mentioned hereinabove. To assist in forming this flattened portion, there is utilized a cylindrical rod or mandrel 180. The tube 140 is bent around this mandrel. To hold the flattened portion in the flattened shape, there are employed the aforementioned clips 148. These clips engage no more than about 5% to 25% of the width of the tube thereby to leave a central portion in flattened position through which fluid may flow under the normal pressure of an intravenous procedure. These clips remain in position in the assembled and installed device, but may be readily remove therefrom for purposes of servicing or substitution or the like. The flattened portion provides a throat constriction which operates generally in the manner shown in FIGS. 7 and 8.

Figure 7:
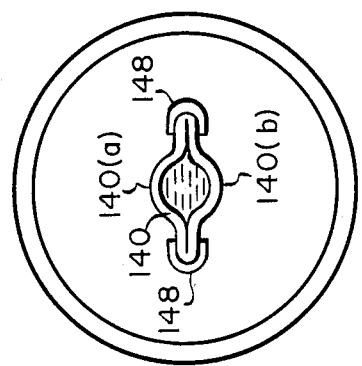
FIG. 7 is a diagrammatic view illustrating the operation of the arrangement of FIG. 4 with fluid flow permitted.
Figure 8:
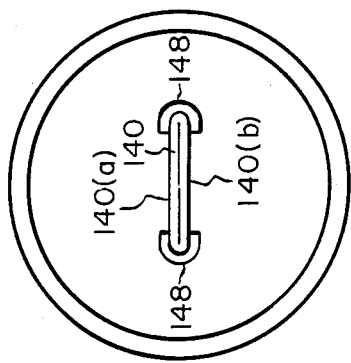
FIG. 8 is a view corresponding to FIG. 7 with flow terminated upon an opening of the system to ambient atmosphere.

With reference to FIGS. 7 and 8, there appears in these FIGS. the support tube 150 and the operative tubular structure 140 as well as clips 148, all of this structure being diagrammatically shown in order to establish an explanation of the operation of the system. In FIG. 7, normal fluid pressure exerted by the pump 120 referred to hereinabove in FIG. 3, forces fluid through the tube 140 and between the normally flat faces 140(a) and 140(b) thereof. Since the tube is formed of rubber and since the upstream section 142 tapers downwardly towards this section, the flow of fluid will not be impeded. During this time, clips 148 tend to hold the central portion 146 in flattened condition but in a yieldable manner so that this yieldable constraint will permit the deformation illustrated in FIG. 7 due to the pressure exerted by the pump 120 or even due to the force of gravity acting on the fluid in a system wherein the pump 120 is not employed.

In FIG. 8 is illustrated the situation where, for example, the pump 120 is not operating or the catheter 126 has become detached from the pump 120 and is opened to ambient atmosphere. In this case, the relative negative pressure in the vascular system as compared with ambient atmosphere causes a suction to be applied to the central portion 146 of the tubular structure 140 thereby to cause a sucking of the faces 140(a) and 140(b) together thereby to form a lock against the penetration of air thereby to prevent air bubbles from entering into the vascular system and thereby to ensure against the formation of air embolisms or the like in the vascular system as might cause serious harm to the patient being treated.

FIG. 9 illustrates a typical blood circulation system 200 for use in connection with open heart surgery. This system is representative of the numerous applications for use of the novel valve and catheter means of the invention. After the beating of the heart 202 is stopped by potassium injection, a catheter 204 is inserted into the right atrium of the heart 202 to drain blood therefrom. This catheter includes fluid flow control means 206 preferably in the form of a one way valve which allows blood to drain from the heart, but which prevents reflux of blood back into the heart. The valve 206 also prevents air from being introduced into the heart through the catheter 204. This valve 206 may be attached to the catheter 204 by way of Luer lock or similar connection means, or it may be an integral part of the catheter 204 itself. This feature of the invention will be explained in greater detail hereinbelow.

At the exit of the valve 206, the blood drains through tubing 208 into an oxygenator apparatus 210 also known as a heart-lung machine. As is well known by those skilled in the art, the oxygenator introduces oxygen into the blood before pumping it back to the patient, thus maintaining circulation of blood while the doctor is operating on the patient's heart. The blood leaving the oxygenator 210 passes through a perfusion safety valve 212 such as is disclosed in U.S. Pat. No. 3,717,174 to Dewall. This valve is responsive to the exhaustion of blood in the oxygenator to automatically stop the flow of blood to the patient thus preventing the pumping of air into the patient's arterial system. After passing through this valve 212, the blood is directed to pump 214, then through tubing 216, back to the patient. Tubing 216 connects to a second catheter 218 which also includes an integral or attached fluid flow control means or valve 220. Valve 220 allows oxygenated blood to flow into catheter 218 and into the patient's artery but prevents both the reflux of blood from the patient back through the catheter as well as the introduction of air into the patient's vascular system.

While the perfusion safety valve 212 mentioned above prevents air from being directed to the catheter 218 in the event of a problem with the oxygenator or heart-lung machine 210, that valve 212 is ineffective for preventing air introduction into the patient in the event of an accidental disengagement of tubing 216 from catheter 218. Thus, in accordance with the invention, valve 220 which is attached directly to catheter 218 in a manner to avoid easy disconnection. Thus, the valve 220 is attached to the catheter 218 by a locking mechanism, such as a Luer lock, or is made integral with catheter 218. This prevents the accidental introduction of air into the patient upon an accidental detachment of the tubing from the catheter. Such an arrangement also prevents the introduction of air into the patient due to the situation where air is introduced into tubing 216, pump 214, or other items which are downstream to the perfusion safety valve 212.

Since this system cannot immediately start up due to lack of sufficient quantity of oxygenated blood to return to the patient, the return line 216 is provided with a Y connection 222 and shunt 224 which allow the fluid to initially return to the oxygenator 210, thus enabling a sufficient resovoir of blood to accumulate therein. This shunt 224 is provided with a one-way valve 226 which allows the blood to flow to the oxygenator 210, but prevents the reflux of blood or air back into the line 216 which carries oxygenated blood to catheter 218. Preferably, this Y connection 222 is located as close to valve 220 and catheter 218 as possible.

Figure 10:
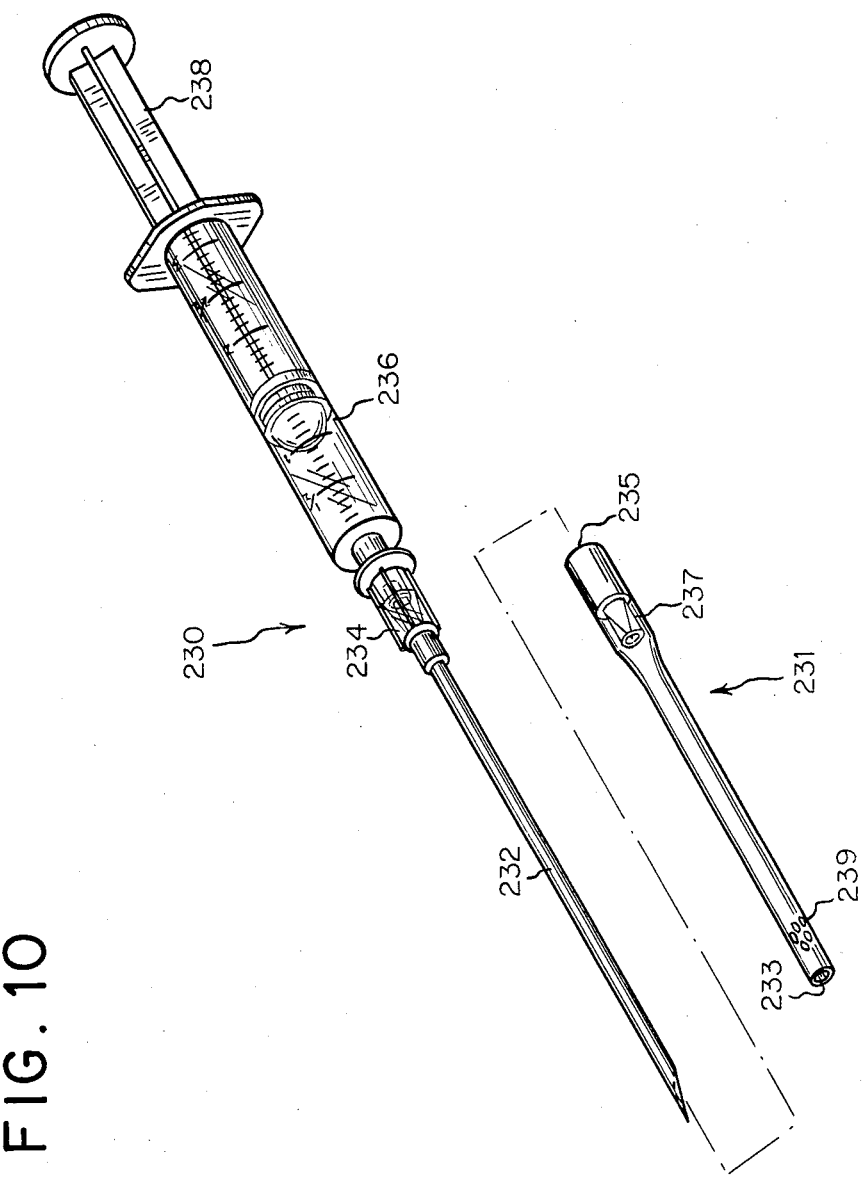
FIG. 10 is a perspective view of a needle and catheter arrangement for injecting fluids into the vascular system of a patient.

To stop the beating of the heart, a solution of potassium is injected into the root of the aorta. This may be accomplished throught the use of a needle and valve arrangement 230 as shown in FIG. 10. There, a standalone needle 232 having an integral one-way valve 234 as described previously for preventing the introduction of air into the patient. Valve 234 is shown as an integral part of the needle, but in an alternate embodiment, it can be attached by a locking mechanism such as a Luer lock to the end of the needle. Attached to the valve and needle is a graduated compartment 236 which would contain the potassium solution that is to be injected. The plunger mechanism 238 is depressed to force the fluid through the valve 234 and needle 232 into the patient. After the plunger mechanism 238 is depressed, the valve 232 then prevents air from entering the patient, and prevents the reflux of blood through the needle 232 into the graduated portion 236 of the arrangement 230. Thus, the valve 234 prevents exsanguination into the graduated cylinder 236.

When fluids are to be repeatedly introduced into the patient, the needle and valve arrangement 230 may be used in conjunction with an indwelling catheter 231. This catheter 231 includes an opening 233 for passage of the needle 230, and includes a mouth 235 for attachment to the area below valve 234 of needle 230. In normal operation, the catheter 231 is positioned upon the needle 230 and both are inserted together into the patient. After the fluid is introduced from the graduated compartment 236, the needle 230 is removed while the catheter 231 is left in the patient.

This catheter 231 includes one way valve 237 which prevents blood flow from the patient, and which also prevents the entry of air thereinto. The introduction of needle 232 into catheter 231 thus obturates valve 237, rendering it incompetent. After the needle 232 is removed, the valve 237 closes and again becomes competent. The end of catheter 231 is provided with holes 239. In the event a blood sample is required, an obturator is placed into valve 237, and holes 239 allow blood to flow into and up the catheter. After the blood sample is obtained, the valve 237 then again becomes competent. The use of this needle 230 and catheter 231 arrangement prevents multiple punctures of the patient's vein or artery, since the catheter 231 maintains its position in the patient and can be reused for introducing additional fluids.

In FIGS. 11 and 12, there is illustrated a catheter and valve arrangement 240 which is useful for draining blood from the patient's heart. FIG. 11 illustrates a catheter 241 having an open end 242 and a plurality of holes 244 which allow the blood from the heart to enter the catheter 241. An integral part of the catheter is the one-way valve 246 which allows blood to flow out but does not allow air or blood reflux back into the catheter 241. A drain-line 248 is shown attached to the catheter and this drain would be directed to an oxygenator 210, as shown in FIG. 9.

FIG. 13 shows an alternate embodiment for the valve end of this catheter 241 in that the valve 246 is provided with connections 250 and 252 for attachment to the catheter 241 and the drainline 248, respectively. In this invention, it is contemplated that either or both of these connections 250, 252 can be male or female. Thus, the valve 246 may have two male connections or two female connections or one of each to match corresponding catheters and/or tubes. In a preferred arrangement, the end of the valve which allows blood to flow out of the valve can be made as a male connection whereas the end of the valve which allows blood into the valve can be a female connection. In this manner, the valve connections will properly orient the valve to allow fluid flow in a particular direction, thus preventing the introduction of air and/or reflux of fluids in the opposite direction. To further illustrate this point, all drainage catheters could be provided with a male connection and all drainage tube lines with a female connection. Therefore, there can only be one specific orientation for the valve, i.e. that of allowing blood to drain from the catheter while preventing air introduction or blood reflux. As mentioned previously, these connections can be of the Leur lock type, because they allow fast connection while avoiding accidental disengagement.

In FIGS. 14 and 15, there is illustrated a catheter and trocar arrangement 250 according to the invention. The trocar portion of this arrangement 250 includes a strong, sturdy needle 252 and one-way valve 262. The catheter 254 includes a plurality of holes 256, valve 260 and a compartment 264 for reception of the needle 252. In order to place the catheter 254 into the proper location in the patient's vascular system, the catheter and trocar are inserted together. The trocar is provided with a sharp point 266 which assists in puncturing the skin and vein or artery of the patient. Additionally, the needle 252 obturates the catheter valve 260, thus rendering it incompetent so as to allow the person inserting this arrangement into the patient to view blood reflux through the trocar. Trocar valve 262 will allow blood flow from the patient's vascular system without allowing blood reflux or air entry therein.

After determining that the catheter and trocar arrangement 250 is properly located, it is possible to remove the trocar as shown in FIG. 15 to allow for the introduction of fluids through the catheter through compartment 264. Removal of the trocar means allows the valve 260 to become competent, thus preventing blood reflux through the catheter as well as prevent the introduction of the air into the vascular system of the patient. Alternately, the trocar can be attached via tubing 268 or other means for removing a predetermined amount of blood for sampling purposes. Furthermore, while such sampling is being undertaken, the attachment of the tubing 268 to the trocar provides a situation wherein the trocar will be pulled out of the catheter should the tubing be accidentally disengaged, rather than opening the end of the trocar. The removal of the trocar from the catheter renders valve 260 competent and prevents blood flow from the patient as well as prevents the introduction of air into the patient. It is also possible to provide the trocar with an attached valve rather than an integral valve as shown.

Another embodiment of this concept would be the use of a long cannula for insertion into the heart of the patient through a leg vein. After the catheter is introduced into the patient the heart of the patient from the leg, it may not be positioned properly.

The catheter hub includes a one-way valve which prevents the reflux of blood. Thereafter, a stiffer reinforcing member can be inserted through the valve and through the length of the cannula to direct the end of the cannula into the proper position or location within the heart of the patient. Since this reinforcing member is a fairly rigid member which will remain within the cannula to maintain it in the proper position, it should also be provided with a one-way valve for the prevention of blood reflux through the member as well as to prevent the introduction of air into the heart of the patient.

Figure 16:
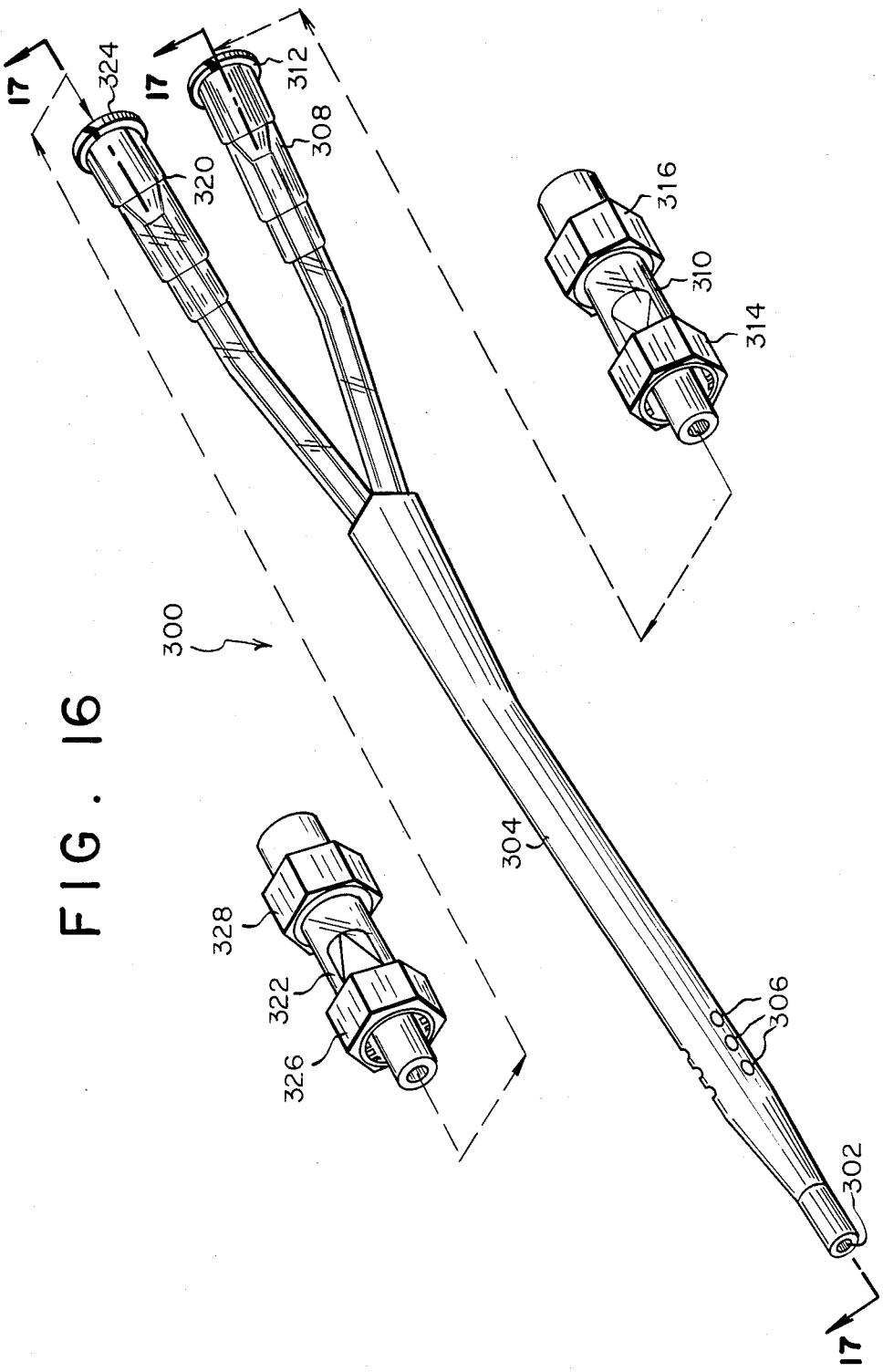
FIG. 16 is a perspective view of a dual lumen cannula also illustrating the fluid flow control means of the invention.

In FIGS. 16–19, a dual lumen cannula for use in dialysis or the like is illustrated. FIG. 16 shows the cannula 300 having an open tip 302 and an elongated body 304. Tip 302 introduces fluids into the vein of the patient, while the plurality of holes 306 on the elongated body 304 allow for the removal of fluids from the patient. Accordingly, the fluid inlet portion of the cannula 308 is provided with a one-way valve 310 which is connected by way of a locking flange 312 and cap 314 arrangement, which is similar to a Luer lock. The opposite end of the valve 310 includes a second locking connection 316 for attachment to tubing or the like. On the outlet portion of the cannula 320 there is attached a one-way outlet valve 322 again having a locking arrangement comprising flange 324 and cap 326. The outlet of this valve also provides a second lock 328 for connection to tubing or the like. The outlet of valve 322 goes directly to the dialysis machine through tubing while the inlet valve 310 is connected to the purified blood line from the dialysis machine. The inlet valve 310 prevents the introduction of air upon an accidental detachment of the purified blood line or due to the incorporation of air into the line due to failure of any of the components of the dialysis machine, while the outlet valve 322 prevents blood reflux back into the patient's system as well as the introduction of air therein.

FIG. 17 illustrates a cross-sectional view of the double lumen dialysis catheter of FIG. 16, however, the valves 332, 336 are shown as integral with the catheter 330 rather than being separately attached as in FIG. 16. Thus, inlet valve 332 is held in place by the connecting line 334 while outlet valve 336 is held in place by outlet tubing 338. The other numerals identifying portions of this drawing figure are the same as those used in FIG. 16.

FIG. 18 is a view of an alternate embodiment for the tip of the catheter of FIGS. 16 and 17. In this arrangement is seen that the body of the catheter is divided into two portions as shown in FIG. 19. One portion which utilizes the tip opening and some of the plurality of side openings, is used for introducing fluid into the patient, where as the remaining portion of side holes are used for removal of fluid. This type of design may be preferred in certain applications.

Figure 20:
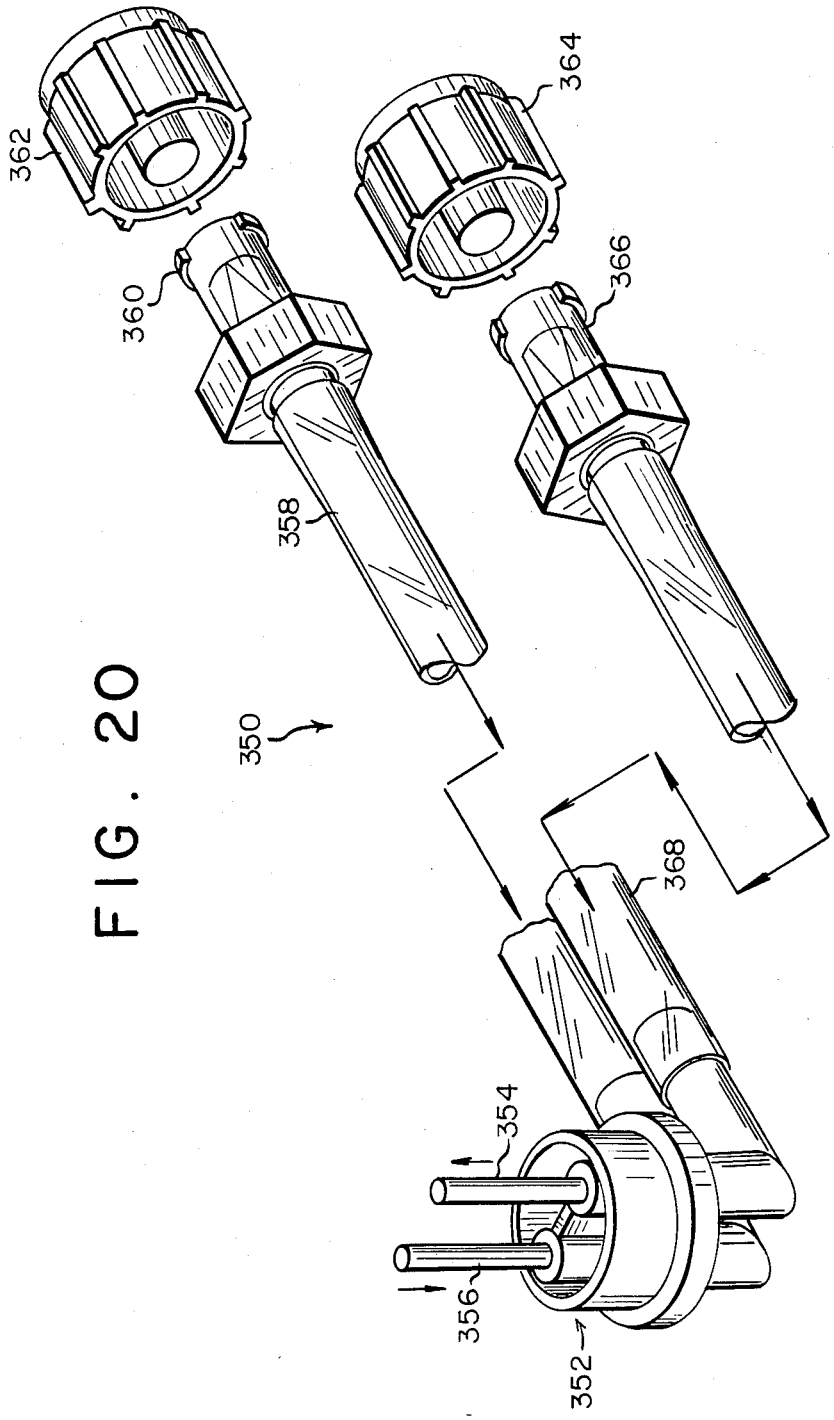
FIG. 20 is a perspective view partially broken away of a double cannula hemodialysis system.

FIG. 20 illustrates an alternate embodiment for a dialysis apparatus 350. This device is used in connection with a patient who has a shunt permanently mounted in a vein located in their forearm or leg. When dialysis is necessary, the patient visits a dialysis center and the device 350 is connected to the shunt in the patient's arm by way of connection 352. This connection 352 has a blood inlet cannula 354 and a blood outlet cannula 356 for the delivery and removal of blood, respectively. Outlet cannula 356 takes blood to be dialized and directs it through tubing 358 and through valve 360 to the matching attachment on the dialysis machine 362. After the blood has been dialyzed, it returns from the machine through fitting 364, valve 366 and tubing 368 before passing through inlet cannula 354 back into the patient. As in the preceding embodiments, valve 360 prevents the introduction of air back into the patient whereas valve 366 prevents reflux of blood or air back into the patient's system.

Having the benefit of the previous disclosure before them, one skilled in the art would be capable of devising numerous alternate arrangements of valves and catheters according to the invention. In this regard, a number of alternate embodiments will be referred to below.

The heart drainage catheter of FIG. 10 with a slight modification could be used to drain fluids from the pleural cavity of the body. This catheter with the valve attachment will allow the fluid to drain but will prevent the reflux of fluid back into the body without the use of clamps or other devices. An example of drainage from the pleural cavity would be a chest tube for removal of fluids from the chest. Another example would be the drainage of urine from the bladder.

It is also possible to utilize various combinations of these catheters for introducing predetermined amounts of fluids or the like into the body of the patient. Specifically, a first catheter tube could be inserted into the patient and a Y connection inserted into the mouth of the catheter. Then, there would be two entry ports for the delivery of two separate fluids into the body of the patient. Each of these ports would then have the appropriate valves to prevent the introduction of air and/or the reflux of fluids. Alternately, in one of the connections a second catheter trocar means, a balloon catheter or the like could be inserted while the first opening could be used for the introduction of fluids. Alternately, rather than locating the valves in the ports of the catheter they can be placed anywhere along its length.

There will now be obvious to those skilled in the art many modifications and variations of the construction set forth hereinabove. These modifications and variations will not depart from the scope of the invention as defined by the following claims.

We claim:

1. A method for preventing the introduction of ambient air into the vascular system of a patient through catheter means introduced into said vascular system during intravenous or intra-arterial procedures which comprises:

providing the catheter means with fluid flow control means comprising: a tubular structure including input means and output means; each provided with an open bore constituting a flow channel; and further means located between the bores of said input and output means of said tubular structure and having an open and a closed position, said further means providing for a connecting channel between said bores when said further means is in the open position, said further means normally being prestressed to said closed position and being forcible to said open position in response to a positive fluid pressure in the bore of either of said input or output means, said further means being constructed and arranged so as to return to said closed position in response to a removal of positive fluid pressure from said bore containing same;

introducing the catheter into the vascular system of the patient during intravenous or intra-arterial procedures; and introducing a fluid into said patient through said fluid flow control means and catheter means by directing the fluid under a positive pressure above that of ambient air into the bore of the input means of said fluid flow control means so that the fluid flow control means remains competent in response to ambient air pressure in the bore of said input means but which opens in response to said positive fluid pressure to allow flow therethrough, while also preventing the introduction of air into the vascular system of the patient.

2. The method of claim 1 wherein the fluid flow control means is integral with or attached to the catheter means.

3. The method of claim 1 which further comprises utilizing means to maintain the fluid flow control means in an open position to view blood reflux through the catheter means or to facilitate the introduction of obturating means.

4. The method of claim 3 wherein the means to maintain the fluid flow control means in an open position further comprises a second fluid flow control means which remains competent in response to ambient air pressure but which opens in response to a positive fluid pressure above that of ambient air.

5. The method of claim 3 wherein the obturating means comprises second catheter means, trocar means, needle means, or fluid directing means.

6. A method for preventing the reflux of blood from the vascular system of a patient through catheter means introduced into said vascular system during intravenous or intra-arterial procedures which comprises:

providing the catheter means with fluid flow control means comprising: a tubular structure including input means and output means, each provided with an open bore constituting a flow-channel; and further means located between the bores of said input and output means of said tubular structure and having an open and a closed position, said further means providing for a connecting channel between said bores when said further means is in the open position, said further means normally being prestressed to said closed position and being forcible to said open position in response to a positive fluid pressure in the bore of either of said input or output means, said further means being constructed and arranged so as to return to said closed position in response to a removal of positive fluid pressure from said bore containing same;

introducing the catheter into the vascular system of the patient during intravenous or intra-arterial procedures; and introducing a fluid into said patient through said fluid flow control means and catheter means by directing the fluid under a positive pressure above that of ambient air into the bore of the input means of said fluid flow control means so that the fluid flow control means remains competent in response to blood reflux in said output bore and ambient air pressure in said input bore but which opens in response to said positive fluid pressure to allow fluid flow therethrough, while also preventing the inntroduction of air into or the reflux of blood from the vascular system of the patient.

7. The method of claim 6 which further comprises utilizing means to maintain the fluid flow device in an open position to temporarily view blood reflux through the catheter means or to facilitate the introduction of obturating means, trocar means, second catheter means, or fluid directing means into the first catheter means.

8. The method of claim 7 wherein the means to maintain the fluid flow control means in an open position further comprises a second fluid flow control means which remains competent in response to blood reflux and ambient air pressure, but which opens in response to a positive fluid pressure above that of ambient air.

9. The method of claim 7 which further comprises connecting the maintaining means to exterior conduit means such that, in the event the exterior conduit means is disengaged from the patient, the maintaining means is also removed, thus returning the fluid flow control means to a closed position.

10. A method for preventing the reflux of fluids into an organ or the pleural cavity of a patient through fluid directing means utilized for removal of said fluids from the patient which comprises:

providing the fluid directing means with fluid flow control means comprising: a tubular structure including input means and output means, each provided with an open bore constituting a flow channel; and further means located between the bores of said input and output means of said tubular structure and having an open and a closed position, said further means providing for a connecting channel between said bores when said further means is in the open position, said further means normally being prestressed to said closed position and being forcible to said open position in response to a positive fluid pressure in the bore of either of said input or output means, said further means being constructed and arranged so as to return to said closed position in response to a removal of positive fluid pressure from said bore containing same;

introducing the fluid directing means into the organ or pleural cavity of the patient for removal of fluids therefrom; and removing fluid from said organ or pleural cavity of said patient through said fluid flow control means and fluid directing means by directing said fluid under a positive pressure ito the bore of the input means of said fluid flow control means so that the fluid flow control means remains competent in respnse to fluid reflux but which opens in response to said fluid pressure in the patient to facilitate the removal of said fluids by flow therethrough, while also preventing the introduction of air or the reflux of fluid into the organ or pleural cavity of the patient.

11. The method of claim 9 which further comprises periodically utilizing means to maintain the fluid flow device in an open position to facilitate faster removal of said fluid from the patient.

12. Catheter means comprising an elongated body portion for insertion into a patient; at least one integral hub portion adjacent to the body portion; and at least one fluid flow control means located in the body or hub portion or adjacent to the hub portion, which means comprises: a tubular structure including input means and output means, each provided with an open bore constituting a flow channel; and further means located between the bores of said input and output means of said tubular structure and having an open and a closed position, said further means providing for a connecting channel between said bores when said further means is in the open position, said further means normally being prestressed to said closed position and being forcible to said open position in response to a positive fluid pressure in the bore of either of said input or output means, said further means being constructed and arranged so as to return to said closed position in response to a removal of positive fluid pressure from said bore containing same so that the fluid flow control means remains competent in response to ambient air pressure or fluid reflux but which opens in response to a positive fluid pressure above that of ambient air to allow fluid flow through said further means from the bore containing the positive pressure to the other bore, said flow control means capable of passing fluid in either direction depending upon which bore contains the positive fluid pressure.

13. The catheter means of claim 12 wherein the fluid flow control means is releasably secured to the hub portion.

14. The catheter means of claim 12 wherein two integral hub portions are provided and each hub includes fluid flow control means located adjacent thereto.

15. The catheter means of claim 14 wherein each fluid flow control means is releasably secured to its respective hub portion.

16. The catheter means of claim 14 wherein a first hub portion allows the introduction of a fluid into the body of the catheter means and a second hub portion allows a body fluid to be removed from the body of the catheter means; the first hub portion including fluid flow control means which remains competent in response to fluid reflux or ambient air pressure but which opens in response to a positive fluid pressure above that of ambient air; the second hub portion including fluid flow control means which remains competent in response to fluid reflux but which opens in response to fluid pressure in the patient.

17. The catheter means of claim 12 further comprising obturating means for rendering incompetent the fluid flow control means.

18. The catheter means of claim 17 wherein the obturating means is second catheter means, trocar means, needle means, or fluid directing means.

19. The catheter means of claim 17 wherein the obturating means is trocar means and the trocar means includes a fluid flow control means which remains competent in response to blood reflux or ambient air pressure but which opens in response to a positive fluid pressure above that of ambient air.

20. The catheter means of claim 17 wherein the obturating means is trocar means and the trocar means includes a fluid flow control means which remain competent in response to fluid reflux but which opens in response to fluid pressure in the patient.

21. The catheter means of claim 12 wherein the end of the body portion opposite the hub portion includes a plurality of apertures.

22. The catheter means of claim 12 wherein the fluid flow control means is located in the body portion.

23. The catheter means of claim 12 wherein the fluid flow control means is located adjacent to the hub portion.

24. Catheter means comprising an elongated body portion for insertion into a patient; an integral hub portion adjacent to the body portion for introducing fluids into the body portion; and integral fluid flow control means located in the body portion; and integral fluid flow control means located in the body portion adjacent the hub portion which comprises: a tubular structure having input means and output means, each provided with an open bore, and channel means connecting said input and output bores and operating between open and closed positions; and means for retaining a portion of the channel means in a prestressed condition to obturate said channel means so as to maintain the channel means in said closed position; said channel means being forcible to said open position in response to a positive pressure above that of ambient air in one of said bores to facilitate flow therethrough; said retaining means returning said channel means to said closesd position when said positive pressure is removed, so that the control means remains competent in response to blood reflux or ambient air pressure, but which opens in response to a positive fluid pressure above that of ambient air to allow fluid flow there said retaining means from the bore containing the positive pressure to the other bore, said fluid flow control means capable of passing fluid in either direction depending upon which bore contains the positive fluid pressure.

25. Catheter means comprising an elongated body portion for insertion into a patient; an integral hub portion adjacent to the body portion for removal of fluids from the patient through the body portion; and integral fluid flow control means located in the body portion adjacent to the hub portion which comprises: a tubular structure having input means and output means, each provided with an open bore, and channel means connecting said input and output bores and operating between open and closed positions; and means for retaining a portion of the channel means in a prestressed condition to obturate said channel means so as to maintain the channel means in said closed position; said channel means being forcible to said open position in response to a positive pressure above that of ambient air in one of said bores to facilitate flow therethrough; said retaining means returning said channel means to said closed position when said positive pressure is removed, so that control means remains competent in response to fluid reflux but which opens in response to fluid pressure in the patient to allow fluid flow through said further means from the bore containing the positive pressure to the other bore, said flow control means capable of passing fluid in either direction depending upon which bore contains the positive fluid pressure.

26. The catheter means of claim 12 wherein said fluid flow control means further comprises a relatively rigid support tube having spaced ends and provided with a bore within which said tubular structure is partly accommodated, said tubular structure including end portions extending out of the support tube and being rolled over the support tube ends for engagement therewith.

27. The catheter means of claim 26 wherein saidf fluid flow control means further comprises a housing provided with first and second channels of different diameters in coaxial relation to define a shoulder therebetween, said support tube and tubular structure insertable into said first channel and trapping said support tube and tubular structure against said shoulder and a catheter accommodated in said second channel, said plug means and catheter providing passageways coupled through said tubular structure.

28. The catheter means of claim 24 wherein the fluid flow control means further comprises a relatively rigid support' member having spaced ends and an internal bore within which said tubular structure is at least partly accommodated, said input and output bores of said tubular structure including end portions extending out of the support member and being rolled over the support member ends for engagement therewith.

29. The catheter means of claim 28 wherein the fluid flow control means further comprises:
a housing provided with first and second channels of different diameters in coaxial relation to define a shoulder therebetween; said support member and channel means being accommodated in said first channel, and
plug means insertable into said first channel and trapping said support member and channel means against said shoulder.

30. The catheter means of claim 29 wherein said obturating means comprises clip means for retaining said channel means portion in a closed condition in the absence of positive fluid pressure.

31. The catheter menas of claim 25 wherein the fluid flow control means furhter comprises a relatively rigid support member having spaced ends and an internal bore within which said tubular structure is at least partly accommodated, said input and output bores of said tubular structure including end portions extending out of the support member and being rolled over·the support member ends for engagement therewith.

32. The catheter means of claim 31 wherein the fluid flow control means further comprises:
a housing provided with first and second channels of different diameters in coaxial relation to define a shoulder therebetween; said support member and channel means being accommodated in said first channel, and
plug means insertable into said first channel and trapping said support member and channels means against said shoulder.

33. The catheter means of claim 32 wherein said obturating means comprises clip means for retaining said channel means portion in a closed condition in the absence of positive fluid pressure.

* * * * *